US009963438B2

(12) United States Patent
Shibasaki-Kitakawa et al.

(10) Patent No.: US 9,963,438 B2
(45) Date of Patent: May 8, 2018

(54) METHOD FOR THE PRODUCTION OF VITAMIN E WITH A HIGH PURITY, VITAMIN E PRODUCED BY SAID METHOD, AND A COMPOSITION COMPRISING SAID VITAMIN E

(71) Applicant: TOHOKU UNIVERSITY, Miyagi (JP)

(72) Inventors: Naomi Shibasaki-Kitakawa, Miyagi (JP); Kousuke Hiromori, Miyagi (JP); Kousei Kanuma, Miyagi (JP); Tomone Sasayama, Miyagi (JP)

(73) Assignee: TOHOKU UNIVERSITY, Miyagi (JP)

( * ) Notice: Subject to any disclaimer, the term of this patent is extended or adjusted under 35 U.S.C. 154(b) by 0 days. days.

(21) Appl. No.: 15/258,111

(22) Filed: Sep. 7, 2016

(65) Prior Publication Data
US 2017/0334875 A1 Nov. 23, 2017

(30) Foreign Application Priority Data

May 18, 2016 (JP) ................................. 2016-099720

(51) Int. Cl.
*C07D 311/72* (2006.01)
*B01D 15/36* (2006.01)

(52) U.S. Cl.
CPC .......... *C07D 311/72* (2013.01); *B01D 15/362* (2013.01); *B01D 15/363* (2013.01)

(58) Field of Classification Search
CPC ... C07D 311/72; B01D 15/362; B01D 15/363
See application file for complete search history.

(56) References Cited

U.S. PATENT DOCUMENTS 3,122,565 A * 2/1964 Kijima ................. C07D 311/72
549/413

FOREIGN PATENT DOCUMENTS

| JP | 8-100131 | 4/1996 |
| JP | 10-508605 | 8/1998 |
| JP | 2002-3488 | 1/2002 |
| JP | 2002-194381 | 7/2002 |
| JP | 2003-171376 | 6/2003 |
| JP | 2004-305155 | 11/2004 |
| JP | 2005-536191 | 12/2005 |
| JP | 2007-176801 | 7/2007 |
| JP | 2007-521382 | 8/2007 |
| JP | 2009-190989 | 8/2009 |
| WO | 96/14311 | 5/1996 |
| WO | 03/092709 | 11/2003 |
| WO | 2005/051294 | 6/2005 |

OTHER PUBLICATIONS

Hiromori et al., "Selective absorption of free fatty acid using weakly basic anion-exchange resin for vitamin E purification", Tohoku University, The 54th Annual Meeting of the Japan Oil Chemists' Society held on Sep. 8-9, 2015.
Hiromori et al., "Highly purification of vitamin E using weakly anion-exchange resin", 27th Vitamin E Annual Meeting (Kagawa), Oral, Jan. 8, 2016.
Shibasaki-Kitakawa, "Technology for complete utilization of vegetable oils using ion-exchange resins as catalysts and absorbents", Tohoku University, JST New Technology Presentation Meetings held on Jul. 7, 2016.
Takahiro Eitsuka et al., "Down-regulation of telomerase activity in DLD-1 human colorectal adenocarcinoma cells by tocotrienol", Biochemical and Biophysical Research Communications 348 (2006) p. 170-175.
Bharat B. Aggarwal et al., "Tocotrienols, the vitamin E of the 21st century: Its potential against cancer and other chronic diseases", Biochemical Pharmacology 80 (2010) p. 1613-1631.

\* cited by examiner

*Primary Examiner* — Timothy R Rozof
(74) *Attorney, Agent, or Firm* — Wenderoth, Lind & Ponack, L.L.P.

(57) ABSTRACT

A method is provided for manufacturing high-purity vitamin E compounds by selectively separating vitamin E compounds such as tocotrienols and tocopherols from oil raw materials such as deodorized distillate, and more specifically, a method is provided, applying to a rich fraction of vitamin E compounds, for obtaining high-purity vitamin E compounds by separating and removing only free fatty acids contained as impurities. The method comprises a process in which a solution containing vitamin E compounds and free fatty acids is placed in contact with a weakly basic anion exchanger, and the free fatty acids are preferentially adsorbed.

8 Claims, 2 Drawing Sheets

METHOD FOR THE PRODUCTION OF VITAMIN E WITH A HIGH PURITY, VITAMIN E PRODUCED BY SAID METHOD, AND A COMPOSITION COMPRISING SAID VITAMIN E

FIELD OF INVENTION

The invention relates to a method of manufacturing high-purity vitamin E compounds, vitamin E compounds manufactured using that method, and composites containing the vitamin E compounds. The invention also relates to a method for separation and removal of free fatty acids contained as impurities from oil containing vitamin E compounds. In particular, the invention is a method of manufacturing high-purity vitamin E compounds, and it relates to a method of manufacturing vitamin E compounds using ion exchangers.

BACKGROUND OF THE INVENTION

Vitamin E compounds (tocotrienols and tocopherols) are attracting attention as substances with health functionality and high antioxidant activity. In particular, tocotrienols have the same basic structure as tocopherols, but with three double bonds in their side chains, and thus have approximately 50 times higher antioxidant activity than tocopherols (Non-patent Reference 1). Recently, it has been reported that tocotrienols have high bioactivity, such as improvement arteriosclerosis and anti-cancer effects (Non-patent Reference 2), and there are expectations for active use in the pharmaceutical and food fields.

However, whereas tocopherols are contained in a wide-range of vegetable oils such as soy bean, rapeseed, sunflower, corn and so on, tocotrienols are contained at ultra-low concentration in certain vegetable oils such as palm. rice bran and so on. In addition, tocotrienols tend to decompose by oxidation due to the double bonds of their side chains, and easily lose their bioactivity.

Deodorizer distillate (scum oil) discharged in the deodorization process during manufacturing of edible oil is used as the raw material for separating and recovering these vitamin E compounds. Although, in all cases, the amounts of vitamin E compounds contained in scum oil are a few tens of times higher than the crude oil, the main component is free fatty acids, and scum oil also contains triglycerides, sterols and various hydrocarbons.

Therefore, no matter which vitamin E compounds are the target, there needs to be a process for recovering rich fraction of vitamin E compounds (corresponding to rough fractionation of vitamin E compounds) separated from raw materials, and a process for obtaining high-purity vitamin E compounds by further separating vitamin E compounds in the recovered solution from other contaminants. Various chromatographic separation methods have been proposed for the latter high-level separation process, and when necessary it is possible to separate the α, β, γ and δ isomers of tocopherol and tocotrienol by trying them chromatographic separation method.

However, for the rich fraction of vitamin E compounds recovered in the former process: the content of vitamin E compounds is low, the amount of contaminants such as free fatty acids is much, and (as issues specific to the chromatographic separation) it requires a large amount of eluent and a long elution-operative time, as specific issues to the chromatographic separation. As results, the production cost and environmental load of the waste liquid had increasingly been problems. Regarding the recovery process for vitamin E compounds, various studies have previously been carrying out focusing on tocopherols. For example, the molecular distillation method has already reached the stage of industrialization.

However, if the molecular distillation method is applied to deodorizer distillate derived from rice bran or palm containing tocotrienols, there is a large thermal decomposition loss due to distillation. Thus there was a problem because the recovered amount of tocotrienol and its purity were extremely low. (Japanese Unexamined Patent Application Publication No. 1996-100131, Japanese Unexamined Patent Application Publication (Translation of PCT Application) No. 1998-508605, Japanese Unexamined Patent Application Publication No. 2002-194381, Japanese Unexamined Patent Application Publication No. 2002-3488, Japanese Unexamined Patent Application Publication No. 2003-171376, Japanese Unexamined Patent Application Publication No. 2004-305155, Japanese Unexamined Patent Application Publication No. 2005-536191, Japanese Unexamined Patent Application Publication No. 2007-521382, Japanese Unexamined Patent Application Publication No. 2007-176801).

On the other hand, the inventors have developed a method for simultaneously producing tocotrienols and biodiesel fuel from fats and oils (Patent Reference 1). Patent Reference 1 discloses a method for manufacturing vitamin E compounds from the fats and oils, including separation by adsorption of vitamin E compounds contained in fats and oils to an anion exchanger, and thereafter, desorption and recovery from the anion exchanger. This method requires no molecular distillation process, and thus can prevent decomposition of vitamin E compounds such as tocotrienols.

However, the method disclosed in Patent Reference 1 had the problem that free fatty acids remained as impurities in the rich fraction of vitamin E compounds.

PRIOR ART REFERENCES

[Patent Reference 1] Japanese Unexamined Patent Application Publication No. 2009-190989

Non-Patent References

[Non-patent Reference 1] Biochem. Biophys. Res. Commun., 348, 170 (2006)

[Non-patent Reference 2] Biochem. Pharmacol., 80, 1613-1631 (2010)

SUMMARY OF THE INVENTION

The purpose of the invention is to provide a method of manufacturing high-purity vitamin E compounds, by selectively separating vitamin E compounds such as tocotrienols from the deodorized distillated indicated above and other oil raw materials. In particular, the purpose is to provide a method of manufacturing high-purity vitamin E compounds by selectively separating and removing only free fatty acids from the rich fraction of vitamin E compounds (crude fraction of vitamin E compounds) recovered from the raw material.

Means for Solving the Problem

More specifically, the invention provides the following inventions:

[1] A manufacturing method for high-purity vitamin E compound(s) characterized by comprising a process in which a solution containing vitamin E compound(s) and free fatty acid(s) is placed in contact with a weakly basic anion exchanger, and the free fatty acid(s) is preferentially adsorbed on the anion exchanger.

[2] The manufacturing method for high-purity vitamin E compound(s) described in item 1 above, wherein the weakly basic anion exchanger is used a weakly basic anion exchange resin whose pKa of a functional group is 7-9.

[3] The manufacturing method for high-purity vitamin E compound(s) described in item 1 or 2 above, wherein the free fatty acid(s) is comprised one or a plurality of organic acids selected from a group consisted of the carbon number range 1-30.

[4] The manufacturing method for high-purity vitamin E compound(s) described in one of the items 1, 2, and 3 above, wherein the oil is used at least one selected from the group consisted of deodorizer distillate (scum oil), fatty acid oil, dark oil, crude oil, and edible oil is used.

[5] The manufacturing method for high-purity vitamin E compound(s) described in one of the items 1-4 above, farther comprising; a process in which a rich fraction of vitamin E compound(s) is obtained, wherein the vitamin E compound(s) contained in oil is adsorbed to a strongly basic ion exchanger and then desorbed from the strongly basic anion exchanger.

[6] The manufacturing method for high-purity vitamin E compound(s) described in item 5 above, wherein esterification of free fatty acid(s) contained in oil is performed using a strongly acidic cation exchanger before adsorption and desorption of vitamin E compounds contained in oil, to and from the strongly basic anion exchanger.

[7] The manufacturing method for high-purity vitamin E compound(s) described in one of the items 1-6 above, wherein each reaction is carried out continuously using reactors filled with a strongly acidic cation exchanger, strongly basic anion exchanger, and/or a weakly basic anion exchange resin.

[8] High-purity vitamin E compound(s) manufactured using the manufacturing methods described in any of the items 1-7 above.

[9] Composites containing the high-purity vitamin E compound(s) described in item 8 above.

[10] A method of separating and removing free fatty acid(s), characterized by being a method for separating and removing free fatty acid(s) contained as impurities from oils containing vitamin E compound(s), and by bringing the aforementioned oil containing vitamin E compound(s) into contact with a weakly basic anion exchanger, and preferentially adsorbing the aforementioned free fatty acid(s) to the weakly basic anion exchanger.

Effects of the Invention

The method of the invention has advantages such as: free fatty acids are adsorbed selectively from the rich fraction of vitamin E compounds to the weakly basic anion exchanger and thus there is little loss of vitamin E compounds, and the free fatty acids whose content in foods is strictly restricted are completely removed, and consequently the treated solution can be used for food products.

In addition, with the method of the invention, essentially only free fatty acids are completely removed from the rich fraction of vitamin E compounds, and it is possible to obtain high-purity vitamin E compounds.

Also, the method of the invention enables easy, continuous operation, and vitamin E compounds can be manufactured on a large-scale, and refined to high purity.

DETAILED EXPLANATION OF THE INVENTION

Description of the Embodiments

Figure 1:
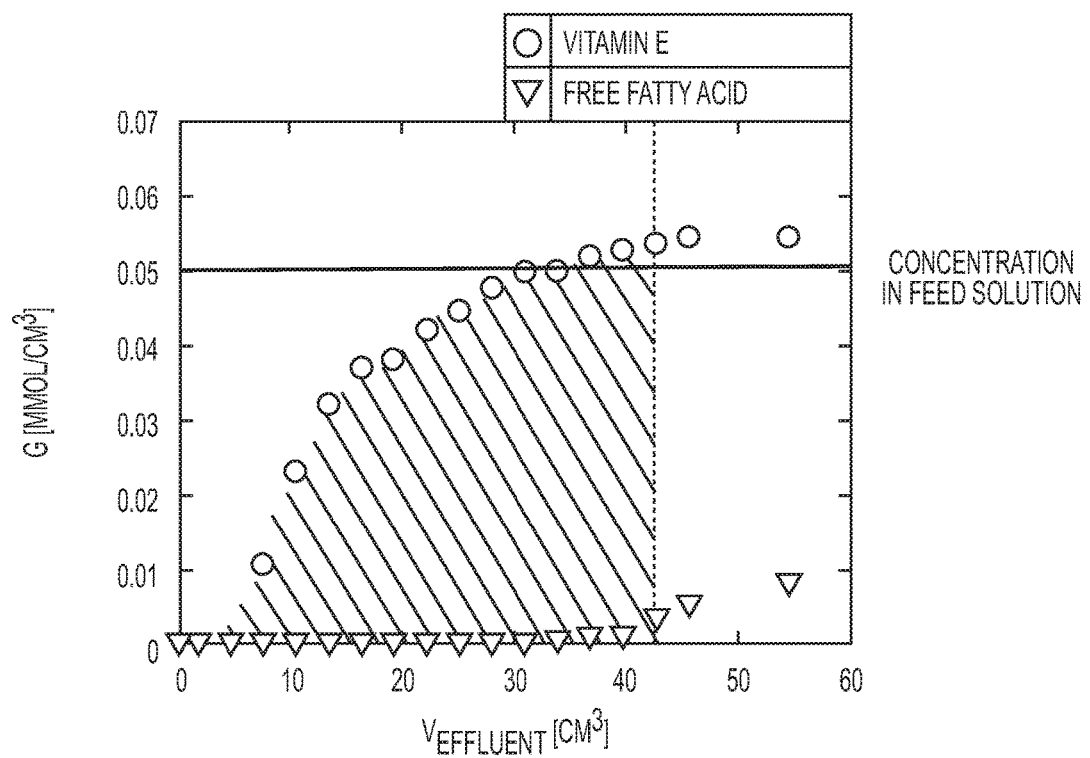
FIG. 1 shows results of an adsorption experiment when a mixed solution of vitamin E and free fatty acids was supplied at a linear velocity of 1.0 cm/min to a column filled with weakly basic anion exchange resin (highly porous type WA21J).

The invention provides a manufacturing method for high-purity vitamin E compounds characterized by comprising a process in which a solution containing vitamin E compounds and free fatty acids is placed into contact with a weakly basic anion exchanger, and the free fatty acids are preferentially adsorbed on the anion exchanger.

Also, the invention is a method for separating and removing free fatty acids contained as impurities from the rich fraction of vitamin E compounds obtained from oil containing vitamin E compounds, and it provides a method for separating and removing free fatty acids characterized by essentially bringing the rich fraction of vitamin E compounds into contact with the weakly basic ion exchanger, and preferentially adsorbing the free fatty acids.

Using the above method, the invention can provide a method for separating and removing free fatty acids contained as impurities from the rich fraction of vitamin E compounds obtained from oil containing vitamin E compounds. As a result, it is possible to manufacture high-purity vitamin E compounds. That is, it is possible to manufacture high-purity vitamin E compounds which essentially contain no free fatty acids. For example, in Examples, it is possible to manufacture high-purity vitamin E compounds with a vitamin E compound purity of "99.8 wt %." In addition, purity can be increased further by repeating this method, and it can be applied to various products (composites) requiring the addition of high-purity vitamin E compounds. In the invention, "high-purity" of high-purity vitamin E compounds means vitamin E compounds comprising a vitamin E compound with content of at least 80% and or more, and indicates the content (wt %) of vitamin E compounds with respect to the total weight excluding solvent but including vitamin E compounds and residual impurity components derived from raw materials other than vitamin E compounds. In the invention, for "high-purity vitamin E compounds," a method is provided for manufacturing vitamin E compounds having, in terms of vitamin E compound content, purity of at least 80%, preferably 85% of higher, more preferably 90% or higher, and still more desirably 95% or higher.

For the method of the invention, it was noticed there is a difference in acidity between vitamin E compounds with low acidity and free fatty acids with high acidity, and a method was discovered for selectively removing free fatty acids from the rich fraction of vitamin E compounds. That is, as a means of selectively removing free fatty acids from the rich fraction of vitamin E compounds, a method was discovered for selectively removing free fatty acids from the rich fraction of vitamin E compounds by using, for example, a weakly basic anion exchanger (resin) with pKa of a functional group in the range 5-12, or preferably the range 7-9.

Here, it is preferable if the anion exchanger has high surface area and exchange capacity. Also, if anion exchange resins are classified based on degree of cross-linkage or porosity, the categories include the gel type, porous type, and highly porous type and so on. However, in the present invention, the method is acceptable in any of these types, and furthermore, the porous and highly porous types with large surface area are preferred for use. As the functional group of the weakly basic anion exchange resin, it is possible, for example, to use groups such as polyamine and dimethylamine and so on.

Well-known weakly basic anion exchange resins of this type can applied. Examples of commercial products include Diaion WA10, WA20, WA21J, WA30 (made by Mitsubishi Chemical Corporation), Lewatit MP-62, VPOC 1065 (made by Lanxess), Amberlite IRA-478, IRA-68, IRA-96, IRA-98, XE-583, Amberlyst A21, Duolite A7, A568, Dowex 66, M-43, Monosphere 66, 77, and Marathon WBA (made by The Dow Chemical Company).

In the present invention, the type (kind) of free fatty acid(s) is, not limited, listed from fatty acids contained in fats and oils containing vitamin E compounds. For example, as free fatty acids, it is possible to list organic acids with a carbon number selected from 1-30. In many cases, free fatty acids contain at least one type (species) of organic acid with a carbon number selected from 1-30.

As typical examples of free fatty acids, oleic acid, linoleic acid, linolenic acid, palmitic acid, stearic acid, and others can be listed.

Also, there are no limitation on the type of raw material oil, the source it is obtained or derived from, and similar factors, but as long as it contains vitamin E compounds such as tocotrienols or tocopherols, there are no limitation, and the oil may be a natural oil (raw oil), synthetic oil, or a mixture of these. Furthermore, the raw material can also be a modified oil, made by modifying some of these types of oils through treatment such as oxidation or reduction, or a processed oil product whose main components are these oils.

It also possible to use deodorized distillate (scum oil) produced as a by-product in the edible oil refining process, fatty acid oil, dark oil, other similar types of oil, or, crude unrefined oil (raw oil). Furthermore, from the perspective of production volume, it is preferable to use rice bran or palm derived oil when aiming to produce tocotrienols, and to use soy beans, sunflower and rapeseed derived oil when aiming to produce tocopherols.

It is acceptable if the rich fraction of vitamin E compounds in the method of the invention contains an arbitrary amount of vitamin E compounds or free fatty acids, in accordance with factors such as the type of raw material oil and the conditions of the manufacturing process for the rich fraction of vitamin E compounds. For example, as described below, in the rich fraction of vitamin E compounds obtained using the method developed by the inventors themselves, vitamin E compounds and free fatty acids are normally contained with concentrations, respectively, in the range 0.002-0.06 mmol/cm$^3$ and 0.002-0.06 mmol/cm$^3$, and purity of the vitamin E compounds (wt %) obtained with the following Equation 1 is, for example, about 40-80 wt %.

Purity [wt %]=Contained amount of vitamin $E$/(contained amount of vitamin $E$+contained amount of free fatty acids)×100     (Equation 1)

It is acceptable even if the rich fraction of vitamin E compounds contains as impurities, for example, an arbitrary amount of substances other than free fatty acids, such as sterol or squalene. These substances have no toxicity, and thus there is no particular need to remove them, other than to further increase purity of the vitamin E compounds. It is also possible to contain alcohols such as ethanol used in manufacturing the rich fraction of vitamin E compounds, and/or organic acids such as formic acid, acetic acid, and citric acid, or their salts.

There are no limitation on the method of obtaining the rich fraction of vitamin E compounds from oil containing vitamin E compounds. For example, it can be obtained using a method like that described in Patent Reference 1 wherein vitamin E compounds contained in oil are adsorbed and separated to an anion exchanger, in particular a strongly basic anion exchanger, and then later desorbed and recovered from the anion exchanger, or a method wherein recovery is done using molecular distillation.

With the method of the invention, it is also possible to obtain the rich fraction of vitamin E compounds by adsorbing the vitamin E compounds contained in oil to a strongly basic anion exchanger, and then desorb vitamin E compounds from the strongly basic anion exchanger, and separate (distill) the solvent or similar material. As the strongly basic anion exchanger used here, it is possible to use a strongly basic anion exchanger whose functional group has pKa>11 or preferably pKa>13. Incidentally, as commercial products, it is possible to use anion exchange resins like those listed in Patent Reference 1, e.g., well-known anion exchange resins such as Diaion PA-306 (made by Mitsubishi Chemical Corporation), Diaion PA-306S (same manufacturer), Diaion PA-308 (same manufacturer), Diaion HPA-25 (same manufacturer), Dowex 1-X2 (made by The Dow Chemical Company), Amberlite IRA-45 (made by Organo Corporation), or Amberlite IRA-94 (same manufacturer).

Furthermore, free fatty acids are also adsorbed to the anion exchanger, and thus when directly treating oil containing these in large amounts, the free fatty acids also adsorb to the anion exchanger. Therefore, in the process step before adsorbing vitamin E compounds contained in oil to the anion exchanger, it is preferable to perform esterification of free fatty acids contained in oil using a cation exchanger, particularly a strongly acidic cation exchanger. As the cation exchanger, it is possible to use, for example, well-known cation resins such as Diaion PK-208 and PK-208LH (made by Mitsubishi Chemical Corporation).

With the method of the invention, it is possible, as described above, to continuously carry out each reaction, using respective reactors packed with strongly acidic cation exchanger, strongly basic anion exchanger, and weakly basic anion exchanger, or by using respective reactors filled with strongly basic cation exchanger and weakly basic anion exchanger.

Also, in each operation stage of the method of the invention, there are no special limitations on factors such as the batch method (batch system) or continuous method (column reactor system) with regard to the contact system between the reactants and ion exchangers. Possible embodiments include equipment provided with a treatment tank, and equipment which transfers resin with a circulation system or counter-current system.

As the contact method, possibilities include flow (method of feeding liquid into a layer packed bed with ion exchange resin), stirring (method using a stirring tank), fluid (fluid bed reactor), and shaking (shaking type reactor) and so on. Also, at the ports for introducing raw materials and ports for recovering products, it is possible to use a fixed column liquid feed type, expanded bed (expanded bed column), or the batch type. In particular, it is suitable to continuously perform each operation such as reaction or adsorption/separation by using reactors packed with resin.

The conditions/means in each operation in the above method can be selected appropriately from, for example, known approaches like those described in Patent Reference 1. For instance, a person skilled in the art can appropriately set each reaction time (contact time, desorption time) in accordance with factors such as reaction temperature, and amount of ion exchange resin used. For example, with a stirring layer, the process is normally performed for 1-10 hours or preferably for 3-5 hours, and with a flow system, it is performed for 5 minutes-2 hours or preferable for about 10 minutes-1 hour. Reaction temperature is normally 30-60° C. Furthermore, there are no limitation on reaction pressure. Carrying out the process under normal pressure is more convenient for operation, but pressurization to about 1-10 atmospheres is possible if necessary.

Also, as indicated in the Examples, when in a flow system the free fatty acids contained as impurities are separated and removed from the rich fraction of vitamin E compounds, it is possible to supply the rich fraction of vitamin E compounds at a linear velocity of, for example, 1.0 cm/min or less, in particular 0.25 cm/min or less, and thereby completely remove free fatty acids, obtain an alcohol solution of vitamin E compounds which essentially does not contain free fatty acids. In this case, the vitamin E compounds which essentially do not contain free fatty acids can be obtained at a high recovery yield of approximately 55% to approximately 85% relative to the absolute quantity of vitamin E compounds derived from raw materials. In addition, the term "vitamin E compounds which essentially do not contain free fatty acids," indicates items in which the purity of vitamin E compounds is at least approximately 98%, up to approximately 100%, and in Working Example 6, the purity of vitamin E compounds exceeds 99%.

As equipment to implement the method of the invention, it is possible, for example, to use containers (reactors) filled with multiple types of the specified ion exchangers (ion exchange resins). There are no particular limitations on the form of the aforementioned containers, but normally the column system is used. If ion exchange resin is used by filling a column with it, then to prevent breakage due to resin swelling, it is preferable to use a filling layer of an expanded bed column with high porosity.

Here, the term "expanded bed column" refers to a type of system used in the separation refining method where the dissolved target component is adsorbed and recovered to adsorbent particles from a highly viscous fluid or fluid containing solids. The fluid is made to flow upward through the inside of the column, and adsorbent particles with high specific gravity are made to float in a stationary state, and then column chromatography operation is performed in a state where high porosity is maintained. An example is described in the Journal of Chemical Engineering of Japan, Vol. 27, No. 2 (2001), pp. 145-148 and so on. However, to achieve efficient operation, it is preferable to use an upward flow during adsorption operation to feed a mixed solution of oil and alcohol.

EXAMPLES

The following explains the specifics of the invention through examples, but the technical scope of the invention is not constrained in any way by these descriptions. Also, in the following examples, implementation was done according to known ordinary methods by a person skilled in the art, unless specifically indicated otherwise.

Procedure for Adsorption Experiment with Batch System

The δ form (pKa 12.6) (commercial product: Sigma-Aldrich Co.) with the highest bioactivity among tocopherols was used as the vitamin E compound, and oleic acid (pKa 4.8), the most major kinds in vegetable oil, was used as the free fatty acid. Non-poisonous ethanol was used as the solvent because the vitamin E compounds are supplied for food applications. Three types of weakly basic anion exchange resin were used: porous-type WA20, and highly porous-type WA30 and WA21 made by Mitsubishi Chemical Corporation. Swelling treatment was performed using solvent.

An absorption experiment with the batch system was carried out by adding the specified amount of ethanol-swollen OH-type resin to 50 $cm^3$ of ethanol solution containing the specified concentration of vitamin E and free fatty acid, and then thoroughly shaking in a thermal bath at 50° C. At that time, the concentrations of both vitamin E and free fatty acid were set to 0.05 $mmol/cm^3$, and the amount of resin used was set to 10 g (wet condition).

In each experiment, a small amount of solution was collected at each specified time. The vitamin E concentration was measured using a high-performance liquid chromatograph (HPLC) equipped with a fluorescence detector, and the free fatty acid concentration was measured using an HPLC system with UV detector.

Results of Adsorption Experiment with Batch System

TABLE 1

Experiment conditions and results with batch system

| | Example 1 | Example 2 | Example 3 |
|---|---|---|---|
| Weakly basic ion exchange resin | WA20 | WA30 | WA21J |
| Time [min] | 180 | 180 | 180 |
| Vitamin E concentration in solution [mmol/$cm^3$] | 0.044 | 0.045 | 0.044 |
| Free fatty acid concentration in solution [mmol/$cm^3$] | 0.009 | 0.008 | 0.005 |
| Residual ratio of vitamin E in solution [mol %] | 87.8 | 89.0 | 88.2 |
| Residual ratio of free fatty acid in solution [mol %] | 18.8 | 16.2 | 9.2 |
| Purity of vitamin E [wt %] | 87 | 89 | 93 |

*Residual ratio = Concentration after adsorption/Initial concentration × 100

Table 1 shows that, in Example 1 using the porous-type resin WA20, concentration of free fatty acid in the bulk liquid phase after 180 minutes decreased to approximately 19% of the initial value. In Example 2 and 3 where the type of resin was varied, vitamin E concentration was about the same as Example 1, but free fatty acid concentration was lower. As a result, purity of vitamin E increased in Example 3 using WA21J.

Due to the above, when highly porous-type WA21J was used, the residual ratio of free fatty acids decreased while the residual amount of vitamin E maintained a high value, and thus vitamin E had the highest purity. Therefore, it was decided to use this resin in an adsorption experiment with the following column reactor system.

Procedure for Adsorption Experiment with Column Reactor System

Just as in the aforementioned batch system, δ-tocopherol and oleic acid were used as the vitamin E compound and free fatty acid, and ethanol was used as the solvent. WA21J resin was used as the weakly basic anion exchange resin, based on results with the aforementioned batch system. The equipment was composed of a supply solution tank, feed pump, column filled with resin, and a thermal bath. The supply solution tank and column were placed in the thermal bath, and kept at 50° C. A glass column of diameter 1.1 cm was used as the column, and it was filled with 10 g of resin (wet condition). Swelling treatment was performed using solvent.

In the adsorption experiment with the column reactor system, an ethanol solution containing the specified concentrations of vitamin E and free fatty acid was supplied using a pump and up-flow flow from the bottom of the column filled with resin. At that time, the concentrations of vitamin E and free fatty acid were set to 0.05 mmol/cm$^3$, as in the batch system of Examples 1-3, and the linear velocity during supply was set to 1.0-0.25 cm/min. In each experiment, effluent from the column was collected at the specified time interval, and vitamin E and free fatty acid concentration were measured using the same technique as with the batch system.

Results of Adsorption Experiment with Flow System

FIG. 1 shows the results of an adsorption experiment with a linear velocity of 1.1 cm/min. The ordinate is the effluent volume $V_{effluent}$ [cm$^3$], and the abscissa is the concentration $C_i$ [mmol/cm$^3$] of each component in the effluent from the column. The trend was for vitamin E concentration in the effluent to quickly increase after starting supply, and then become constant at a supply solution concentration of 0.05 mmol/cm$^3$. On the other hand, free fatty acid concentration was zero up to an effluent volume of 43 cm$^3$, and after that it gradually increased. Thus, the effluent volume obtained to that point, and the contained amounts of vitamin E and free fatty acid [mmol] were found, taking as the breakthrough point where concentration of free fatty acid in the effluent exceeded 5% of the supply solution concentration. The results are shown in Table 2. Then the recovery yield [%] was calculated, i.e., vitamin E content (purity) [wt %] with respect to the amount of all components, and the amount obtained as high-purity vitamin E with respect to the amount of vitamin E supplied as a mixture to the column.

TABLE 2

Experiment conditions and results with flow system

| | Example 4 | Example 5 | Example 6 |
|---|---|---|---|
| Linear velocity [cm/min] | 1.0 | 0.50 | 0.25 |
| Amount of effluent obtained up to the free fatty acid break [cm$^3$] | 42.7 | 62.7 | 74.9 |
| Vitamin E content in effluent [mmol] | 1.48 | 2.46 | 3.03 |
| Free fatty acid content in effluent [mmol] | 0.012 | 0.032 | 0.012 |
| Vitamin E purity in effluent [wt %] | 97.9 | 98.6 | 99.4 |
| Recovery yield of high-purity product vitamin E (acquisition yield) [%] | 68.1 | 80.7 | 86.2 |

The above shows that, in Example 4 with a linear velocity of 1.0 cm/min, it was possible to obtain a vitamin E solution of purity approximately 98 wt % up to an effluent liquid volume of approximately 43 cm$^3$. Here, vitamin E obtained as a high-purity product exhibited an acquisition ratio of 68% with respect to the amount of vitamin E in the supply solution of raw material. It was confirmed that the remaining 32% flowed out in a mixed condition with free fatty acids, or remained in the column, and there was no material loss of vitamin E by this operation.

Next, values were found in the same way for the results of the adsorption experiment with linear velocity reduced to 0.50 cm/min (Example 5) and 0.25 cm/min (Example 6), and the results are summarized in Table 2 above. When the linear velocity is reduced, the breakthrough point where free fatty acid concentration of the effluent exceeds 5% of the value of the supply solution, was delayed, and thus the obtained volume of effluent increased. In addition, it is evident that under all conditions the purity of vitamin E of the effluent exceeds 98 wt %, and the lower the linear velocity, the greater the amount of vitamin E obtained as high-purity product.

The above results show that it is possible to obtain a high-purity vitamin E solution containing no free fatty acids with a flow system, and the recovery amount (obtained amount) and recovery yield (acquisition yield) can be increased by reducing the supply velocity.

Application of the Invention to Actual Raw Material (e.g., Fats and Oils)

Figure 2:
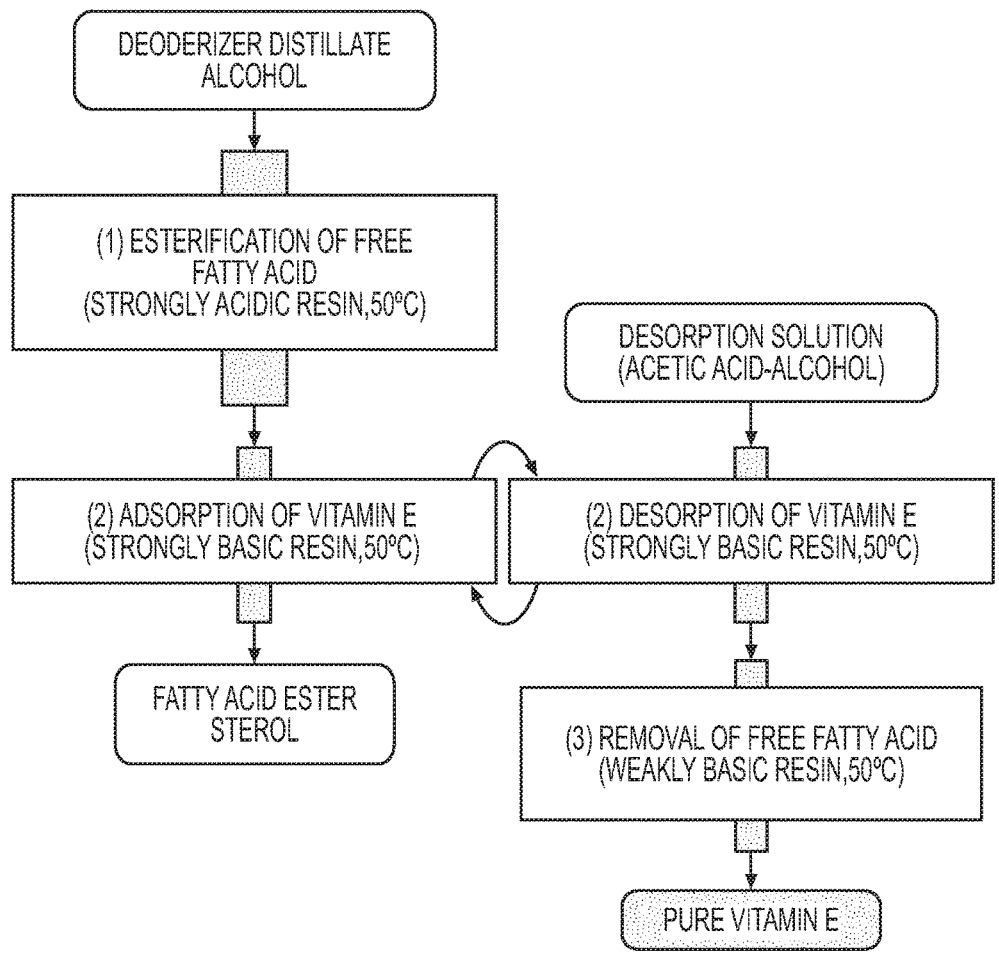
FIG. 2 is schematic drawing showing the manufacturing process, including the process for the method of the invention, in the process for manufacturing vitamin E compounds from fats and oils.

FIG. 2 below shows a schematic diagram of the method of manufacturing vitamin E compounds of the invention, combining: (1) A process of esterification of free fatty acids using a strongly acidic cation exchange resin, (2) A process of adsorption of vitamin E compounds using a strongly basic anion exchange resin, and a process for desorption of vitamin E compounds from the resin, and (3) A process for separation of free fatty acids using a weakly basic anion exchange resin. The process is composed of three processes: (1) A column filled with strongly acidic cation exchange resin for esterification of free fatty acids (FAH) (called the esterification column), (2) A column filled with strongly basic anion exchange resin for adsorption of vitamin E compounds ($V_EH$) (called the adsorption/desorption column), and (3) A column filled with weakly basic anion exchange resin for free fatty acid separation (called the refining column).

The following describes the details of each operation.

In the esterification of free fatty acids in process (1), deodorized distillate derived from rice bran was used. This material was provided by an edible rice oil manufacturing company. The composition of an ordinary deodorizer distillate is shown in Table 3.

TABLE 3

Composition of ordinary deodorized distillate

| Composition | [wt %] |
|---|---|
| Tocopherols | 1.44 |
| Tocotrienols | 1.39 |
| Free fatty acids | 43.8 |
| Hydrocarbons | 31.2 |
| Glycerides | 12.6 |
| Sterols | 4.45 |
| Carbonyl compounds | 3.62 |
| Alcohols | 1.44 |

A strongly acidic cation exchange resin (porous type made by Mitsubishi Chemical Corporation) was used for the resin, and a glass column with inner diameter 5 cm was filled with 675 g of resin (wet condition). After that, the esterification column was kept at 50° C., and a raw material solution with ethanol added to deodorized distillate in the reacting amount relative to the total amount of fatty acid groups of free fatty acids and triglycerides was supplied with an upward flow from the bottom of the column at a flow rate of 1.0 cm$^3$/min. Then the concentration of vitamin E compounds and free fatty acids in effluent from the column was measured using the same technique as that indicated above.

In adsorption of vitamin E compounds in process (2), the esterified deodorizer distillate, which is the effluent of operation (1), was used as is as the supply solution, and for the resin, a strongly basic anion exchange resin (porous type made by Mitsubishi Chemical Corporation) was used as the OH type. The solution tank and reactor were placed in a thermal bath, and kept at 50° C. A glass column (adsorption/desorption column) with inner diameter 1.1 cm and filled with 6.7 g of resin (wet condition) was used as the reactor, and the supply solution was supplied using a pump with an upward flow at a flow rate of 1.0 cm$^3$/min. In this case, vitamin E compounds in the supply solution are retained in the resin. However, if too much raw material solution is supplied, the vitamin E compounds retained in the resin will flow out, and thus this is the optimal condition for the supply amount.

Next, the ethanol was supplied with a downward flow at a flow rate of 1.0 cm$^3$/min to remove the supply solution remaining in the column and containing components other than vitamin E.

Following that, desorption of vitamin E compounds in process (2) and separation of free fatty acids in process (3) are performed simultaneously. Behind the aforementioned adsorption/desorption column, a connection was made with a refining column in which a glass column with inner diameter of 1.1 cm was filled with 10 g (wet condition) of weakly basic anion exchange resin WA21J. Then a 0.43 mol/dm$^3$ acetic acid-ethanol solution was supplied from the top of the concentration column. The flow rate was set to the value 0.25 cm$^3$/min, optimized for the aforementioned flow system. In addition, as a comparative example, an experiment was conducted in the same way, using only the adsorption/desorption column, without connecting a later-stage refining column. In this analysis, the concentrations of vitamin E compounds and free fatty acids in effluent from the column were measured using the same technique as that described above.

Results

Table 4 shows the results of esterification of free fatty acids in process (1). A comparison was done between analysis values for each component concentration in the raw material solution with mixed rice bran deodorizer distillate and ethanol, and the average values when the concentrations of each component of the effluent were became constant. In addition, the residual ratio of each component with respect to the raw material solution were also found. Some free fatty acids remained in the raw material solution after esterification. The conversion ratio due to esterification is extremely high, and only approximately 4% of free fatty acids remained. However, even with this residual ratio, it is evident that tocopherols and tocotrienols are at the same concentration level. As can be seen, the residual ratio for tocotrienols was 100% and there was no loss by thermal decomposition loss. Even tocotrienols, with their low thermal stability, remained at a ratio of 71%.

TABLE 4

Changes in component composition before and after passing through esterification column

| Components | Feed conc. [mmol/cm$^3$] | Effluent conc. [mmol/cm$^3$] | Residual ratio [%] |
| --- | --- | --- | --- |
| Free fatty acids | 0.667 | 0.0247 | 3.7 |
| Tocopherols | 0.0344 | 0.0352 | 102 |
| Tocotrienols | 0.0346 | 0.0246 | 71 |

Table 5 shows the results when desorption of vitamin E compounds in process (2) and separation of free fatty acids in process (3) were performed simultaneously. Here, values were found for the effluent volume up to recovery of 95% of the vitamin E compounds adsorbed to the resin in process (2), and the content [mmol] of vitamin E compounds and free fatty acids. The content of vitamin E compounds with respect to the amount of all components (purity) [wt %] was also calculated.

In Comparative Example 1, when "separation of free fatty acids in process (3)" is "none" (marked with the "x" in Table 5), the purity of vitamin E compounds in the effluent was low at approximately 66%, and free fatty acids were mixed in at approximately 34%. That is, in Comparative Example 1, the content (purity) of vitamin E compounds was approximately 66%, and it is not possible to provide a method of manufacturing vitamin E compounds with the high purity (purity 80% of higher) that can be provided with the method of the invention. In contrast, in Example 7, when "separation of free fatty acids in process (3)" is "applied (used)" (marked with the "o" in Table 5), it is evident that the amount of vitamin E compounds in the effluent exhibited an essentially high purity value of 99.8 wt %.

Based on the above examination, it was found that free fatty acids which remained in the concentration process can be completely removed by adopting a separation method for free fatty acids using a weakly basic anion exchange resin as a new refining process for vitamin E compounds, and combining this with a concentration method based on adsorption/desorption of vitamin E compounds using a strongly basic anion exchange resin. In this case, it was found that 99.8 wt % high-purity products can be obtained without decomposition loss of vitamin E compounds.

TABLE 5

Results of conducting desorption of vitamin E compounds in process (2) and separation of free fatty acids in process (3)

| | Example 7 | Comparative Example 1 |
| --- | --- | --- |
| Desorption of vitamin E compounds in process (2) | o | o |
| Separation of free fatty acids in process (3) | o | x |
| Amount of effluent until 95% of vitamin E adsorbed to adsorption/desorption column can be recovered [cm$^3$] | 63.7 | 30.6 |
| Amount of vitamin E compounds in effluent [mmol] | | |
| Tocopherols | 0.929 | 0.925 |
| Tocotrienols | 0.691 | 0.617 |
| Amount of free fatty acids in effluent [mmol] | 0.006 | 1.160 |
| Purity of vitamin E compounds in effluent [wt %] | 99.8 | 66.2 |

POTENTIAL INDUSTRIAL APPLICATIONS

The invention has, for example, the potential industrial applications indicated below.

(1) The invention enables manufacturing of inexpensive, high-purity natural vitamin E (tocopherols), and thus will allow wider industrial use in areas such as animal feed and food additives.

(2) The invention enables commercial production of tocotrienols, for which it was previously impossible to mass-produce high-purity products.

The invention claimed is:

1. A method of manufacturing a high-purity vitamin E compound comprising contacting a solution comprising a vitamin E compound and a free fatty acid with a weakly basic anion exchanger having a functional group pKa of 7-9, wherein the free fatty acid is adsorbed.

2. The method of claim 1, wherein the weakly basic anion exchanger is a weakly basic anion exchange resin.

3. The method of claim 1, wherein the free fatty acid is at least one organic acid having a carbon number of 1-30.

4. The method of claim 1, wherein the vitamin E compound is contained in at least one oil selected from the group consisting of deodorizer distillate (scum oil), fatty acid oil, dark oil, crude oil, and edible oil.

5. The method of claim 1, further comprising obtaining a rich fraction of vitamin E compound by adsorbing the vitamin E compound contained in an oil to a strongly basic ion exchanger and then desorbing the vitamin E compound from the strongly basic anion exchanger to obtain the rich fraction of vitamin E compound.

6. The method of claim 5, further comprising esterification of free fatty acid contained in the oil by using a strongly acidic cation exchanger before the adsorbing and desorbing of the vitamin E compounds contained in the oil, to and from the strongly basic anion exchanger.

7. The method of claim 1, further comprising a continuous reaction using reactors filled with a strongly acidic cation exchanger, strongly basic anion exchanger, and/or a weakly basic anion exchange resin.

8. A method of separating and removing a free fatty acid contained as an impurity in a vitamin E compound, the method comprising:
    contacting an oil comprising a vitamin E compound with a weakly basic anion exchanger having a functional group pKa of 7-9, and
    adsorbing a free fatty acid to the weakly basic anion exchanger.

* * * * *